United States Patent
Cakic et al.

(10) Patent No.: US 12,029,401 B2
(45) Date of Patent: Jul. 9, 2024

(54) CUTTING TOOL FOR THE HORIZONTAL INCISION OF A TENDON

(71) Applicant: MEDACTA INTERNATIONAL SA, Castel San Pietro (CH)

(72) Inventors: Luka Cakic, Castel San Pietro (CH); Francesco Siccardi, Castel San Pietro (CH); Sascha Berberich, Castel San Pietro (CH); Riccardo Lucchini, Castel San Pietro (CH); Gianluca Parisi, Castel San Pietro (CH)

(73) Assignee: Medacta International SA, Castel San Pietro (CH)

( * ) Notice: Subject to any disclaimer, the term of this patent is extended or adjusted under 35 U.S.C. 154(b) by 776 days.

(21) Appl. No.: 17/276,033

(22) PCT Filed: Jul. 23, 2019

(86) PCT No.: PCT/IB2019/056262
§ 371 (c)(1),
(2) Date: Mar. 12, 2021

(87) PCT Pub. No.: WO2020/053675
PCT Pub. Date: Mar. 19, 2020

(65) Prior Publication Data
US 2022/0047253 A1 Feb. 17, 2022

(30) Foreign Application Priority Data

Sep. 13, 2018 (IT) .......................... 102018000008559

(51) Int. Cl.
A61B 17/00 (2006.01)
A61B 17/3209 (2006.01)

(52) U.S. Cl.
CPC .... *A61B 17/00008* (2013.01); *A61B 17/3209* (2013.01); *A61B 2017/00455* (2013.01);
(Continued)

(58) Field of Classification Search
CPC .......... A61B 17/00008; A61B 17/3209; A61B 2017/00455; A61B 2017/00738; A61B 2017/00969
See application file for complete search history.

(56) References Cited

U.S. PATENT DOCUMENTS 5,391,169 A * 2/1995 McGuire ............ A61B 17/1677
606/86 R
5,601,584 A * 2/1997 Obagi .................. A61B 17/322
606/172

(Continued)

OTHER PUBLICATIONS

International Search Report and Written Opinion for International Application No. PCT/IB2019/056262 dated Nov. 13, 2019, 11 pages.

*Primary Examiner* — Sarah A Long
(74) *Attorney, Agent, or Firm* — Meunier Carlin & Curfman LLC (57) ABSTRACT

Various implementations include a cutting tool for the horizontal incision of tendons. The tool comprises a stem extending along a longitudinal axis, having a distal end, a proximal end and a cutting head, located close to said distal end, having a base plate, having a longitudinal extension axis parallel to the longitudinal axis of the stem, and a blade extending on a plane parallel to the base plate. The blade has a plurality of cutting edges inclined with respect to the longitudinal axis of the cutting head according to different angles, so as to identify at least two vertices defined by two V-shaped profiles.

19 Claims, 6 Drawing Sheets

(52) U.S. Cl.
CPC ............... *A61B 2017/00738* (2013.01); *A61B 2017/00969* (2013.01)

(56) References Cited

U.S. PATENT DOCUMENTS

| | | | |
|---|---|---|---|
| 9,017,354 B2 * | 4/2015 | Fink | A61B 17/32 606/167 |
| 2012/0215240 A1 | 8/2012 | Fink et al. | |
| 2012/0283793 A1 | 11/2012 | Burroughs, III | |

\* cited by examiner

Fig.8

CUTTING TOOL FOR THE HORIZONTAL INCISION OF A TENDON

TECHNICAL FIELD

The present invention concerns a cutting tool for the horizontal incision of a tendon.

PRIOR ART

The cutting tool that is the subject of the present invention is intended for the horizontal incision of the quadriceps tendon, which, as is well known, offers considerable benefits for the reconstruction of the cruciate ligament. In fact, the quadriceps tendon can attain a larger diameter than others, its collection site has a low morbidity compared to e.g. the patellar tendon, it has good biomechanical properties and, since it is less prone to strain or deformation, it has a stiffness profile that is preferable for the reconstruction of the knee ligament.

The surgical technique for cutting and removing the quadriceps tendon involves a cutaneous incision above the upper edge of the patella.

After the subcutaneous dissection, the layers of the prepatellar bursa are longitudinally separated to expose the quadriceps tendon.

Then the tendon is incised with a vertical cutting tool, or tendon strippers, of the desired width for the reconstruction of the cruciate ligament.

Through the cutaneous incision, the cutting tool for the vertical incision is applied to the tendon in a subcutaneous position and pushed proximally onto the tendon until it reaches the desired length for the transplant. Thus, the tendon is not completely severed but incised at the sides.

A second step of the operation involves horizontally cutting the tendon, parallel to the axis of extension of the tendon itself. With this step, the portion of the tendon to be removed is separated from the surrounding soft tissue at the top and at the bottom by means of a second cutting tool. This cutting tool for horizontal incision, also known as a tendon separator, defines the thickness of the tendon to be removed.

Through the cutaneous incision, the cutting tool for horizontal incision or the tendon separator is introduced sideways into the incision of the tendon and subcutaneously pushed along the same length in the proximal direction to horizontally cut the tendon, above and below, along the tendon's direction of extension.

A third stage involves the insertion, again subcutaneously, of a third tool adapted to transversely sever the proximal end of the tendon, where "proximal" refers to the patient.

Finally, the distal end of the tendon is also severed, and then removed and prepared for use in reconstructing the cruciate ligament.

Specifically, the present invention is related to a cutting tool for the horizontal incision of the tendon and therefore pertains to the cutting tool used in the second part of the operation.

The known surgical techniques require an open surgical procedure and the tools used make the process of collecting the tendon itself difficult. Although some of the most modern techniques offer subcutaneous solutions, they still present difficulties because of the design and the methods of using the tool. Some of the disadvantages found in the tools currently used include unsteady cutting tips that lead to uncontrolled and dimensionally inaccurate collections.

Other tools, on the other hand, have cutting heads with a greater resistance to cutting due to the rectangular geometry of the cutting edges.

It was found that even the cutting edge orthogonal to the direction in which the cutting advances, involves difficulties in the incision and risks of damage to the tissue itself.

The purpose of the present invention is to present a cutting tool for the horizontal incision of a tendon that overcomes the drawbacks of the prior art described above.

One of the purposes of the present invention, in fact, is to propose a cutting tool for the horizontal incision of a tendon that is minimally invasive, and that ensures a cut in complete safety for the patient without any damage to the surrounding soft tissue.

Moreover, the purpose of the present invention is to propose a cutting tool for the horizontal incision of a tendon that is easy for the surgeon to use and that allows a fast, safe, steady and precise cut, despite the surgical site's not allowing the surgeon good visibility.

Another purpose of the present invention is to propose a cutting tool for the horizontal incision of a tendon that allows an easy process for collecting the tendon itself as well as preserving the cosmetic aspect after surgery.

These and other purposes are substantially attained by a cutting tool for the horizontal incision of a tendon as described in one or more of the accompanying claims.

SUMMARY

In particular, according to a first aspect, the present invention concerns a cutting tool for the horizontal incision of tendons.

A stem extending along a longitudinal axis, having a distal end, a proximal end and a cutting head, located close to this distal end, is preferably provided.

The cutting head preferably has a base plate, having a longitudinal extension axis parallel to the longitudinal axis of the stem, and a blade extending on a plane parallel to said base plate. The blade preferably has a plurality of cutting edges inclined with respect to the longitudinal axis of said cutting head according to different angles, so as to identify at least two vertices defined by two V-shaped profiles.

Said blade preferably comprises a first distal cutting edge, inclined with respect to the longitudinal axis of said cutting head by an angle comprised between 70° and 80°, preferably 75°.

Said blade preferably comprises a second proximal cutting edge, inclined with respect to the longitudinal axis of said cutting head by an angle comprised between 55° and 65°, preferably 60°.

Said blade preferably comprises a third intermediate cutting edge, interposed between the first distal edge and the second proximal edge and connected to them, inclined with respect to the longitudinal axis of said cutting head by an angle comprised between 100° and 110°, preferably 105°.

Said first distal cutting edge preferably forms an angle comprised between 145° and 155°, preferably 150°, with said third intermediate cutting edge. Said second proximal cutting edge preferably forms an angle comprised between 40° and 50°, preferably 45°, with said third intermediate cutting edge.

The cutting head preferably has a beveled upper edge located at the distal end of the base plate, comprising a blade, adapted to cut the strip of tendon at the top.

Said base plate and said blade are preferably connected together only by means of a side wall orthogonal to both and projecting from one side of the base plate.

Advantageously, the cutting head lies on a plane parallel to the longitudinal axis of said stem and is connected to the latter by means of a fitting inclined with respect to the longitudinal axis by an angle comprised between 10° and 20°, preferably 15°. The lying plane of the cutting head is staggered and parallel to the lying plane of the stem.

The cutting head, in use, is preferably located below the longitudinal axis of the stem.

The cutting edges of the blade and the upper blade each preferably have beveled edges.

In use, the cutting head preferably has a C-shaped cross-section.

The stem is preferably integral with said cutting head.

The stem can preferably be coupled to a gripping handpiece to facilitate the surgeon's grip.

The stem preferably has a notch for steady coupling to the gripping sleeve.

The stem preferably also has a flat surface to avoid relative rotation between the stem and the gripping sleeve.

The stem preferably has a graduated scale along its longitudinal extension.

The stem preferably has an orientation indicator to help correctly align it with the gripping handpiece and correctly insert the tool into the surgical site.

Additional features and advantages will emerge in greater detail in the description of a preferred, but not exclusive, embodiment of a cutting tool for the horizontal incision of a tendon, according to the present invention and the dependent claims.

BRIEF DESCRIPTION OF THE DRAWINGS

The present invention will be made clearer by the following detailed description, with reference to the attached drawings provided by way of example only, in which.

DETAILED DESCRIPTION

In the above figures, the number 1 designates in its entirety a cutting tool for the horizontal incision of a tendon, according to the present invention. In the example shown, the tool 1 is suitable for being used during the performance of surgery in which the quadriceps tendon is removed from its anatomical site to be implanted at another site for the reconstruction of the cruciate ligament.

The cutting tool 1 comprises a stem 2 that extends along a longitudinal axis 2a and that has a distal end 2d and a proximal end 2p.

The terms "distal" and "proximal" indicate proximity with respect to the surgeon. Therefore, the "proximal" end is the one closest to the surgeon's hand, while the "distal" end is the one furthest from the surgeon's hand. The proximal end 2p can be connected to a gripping sleeve 4 that acts as the grip of the cutting tool 1. Close to the proximal end 2p, the stem 2 has a notch 5 for the steady coupling of the stem 2 itself with the locking mechanism of the gripping sleeve 4. In this way, after coupling, axial sliding along the axis 2a between the gripping sleeve 4 and the stem 2 is prevented.

At the proximal end 2p, moreover, the stem 2 has a flat surface 6 that couples with an abutment inside the gripping sleeve 4, to avoid relative rotation between the stem 2 and the gripping sleeve 4 itself around the longitudinal axis 2a.

The stem 2 has a graduated scale 7 along the longitudinal extension of the side surface 2c, so as to have a reference regarding the depth of insertion of the tool into the skin, to know to what depth to make the cut, and to have an indication of the length of collection and, therefore, of the length of soft tissue to be collected.

Near the proximal end 2p there is also an orientation indicator 8 to help the correct alignment with the gripping handpiece 4 and the correct insertion of the tool 1 inside the surgical site.

Close to the distal end 2d, the cutting tool 1 also comprises a cutting head 9 having a plurality of blades 11, 15.

Specifically, the cutting head 9 has a flat horizontal base plate 10, the longitudinal axis 9a of which is parallel to the longitudinal axis 2a of the stem 2, and a blade 11 extending on a plane parallel to the base plate 10. The blade 11 has a geometry that defines two Vs and has a plurality of cutting edges 11a, 11b, 11c inclined with respect to the longitudinal axis 9a of the cutting head 9 according to different angles.

In particular, the blade 11 comprises a first distal cutting edge 11a inclined with respect to the longitudinal axis 9a of the cutting head 9 by an angle α comprised between 70° and 80°, preferably of 75°.

The blade 11 also comprises a second proximal cutting edge 11b inclined with respect to the longitudinal axis 9a of said cutting head 9 by an angle β comprised between 55° and 65°, preferably of 60°.

Finally, the blade 11 comprises a third intermediate cutting edge 11c, interposed between the first distal edge 11a and the second proximal edge 11b and connected to them, inclined with respect to the longitudinal axis 9a of said cutting head 9 by an angle γ comprised between 100° and 110°, preferably of 105°.

Figure 8:
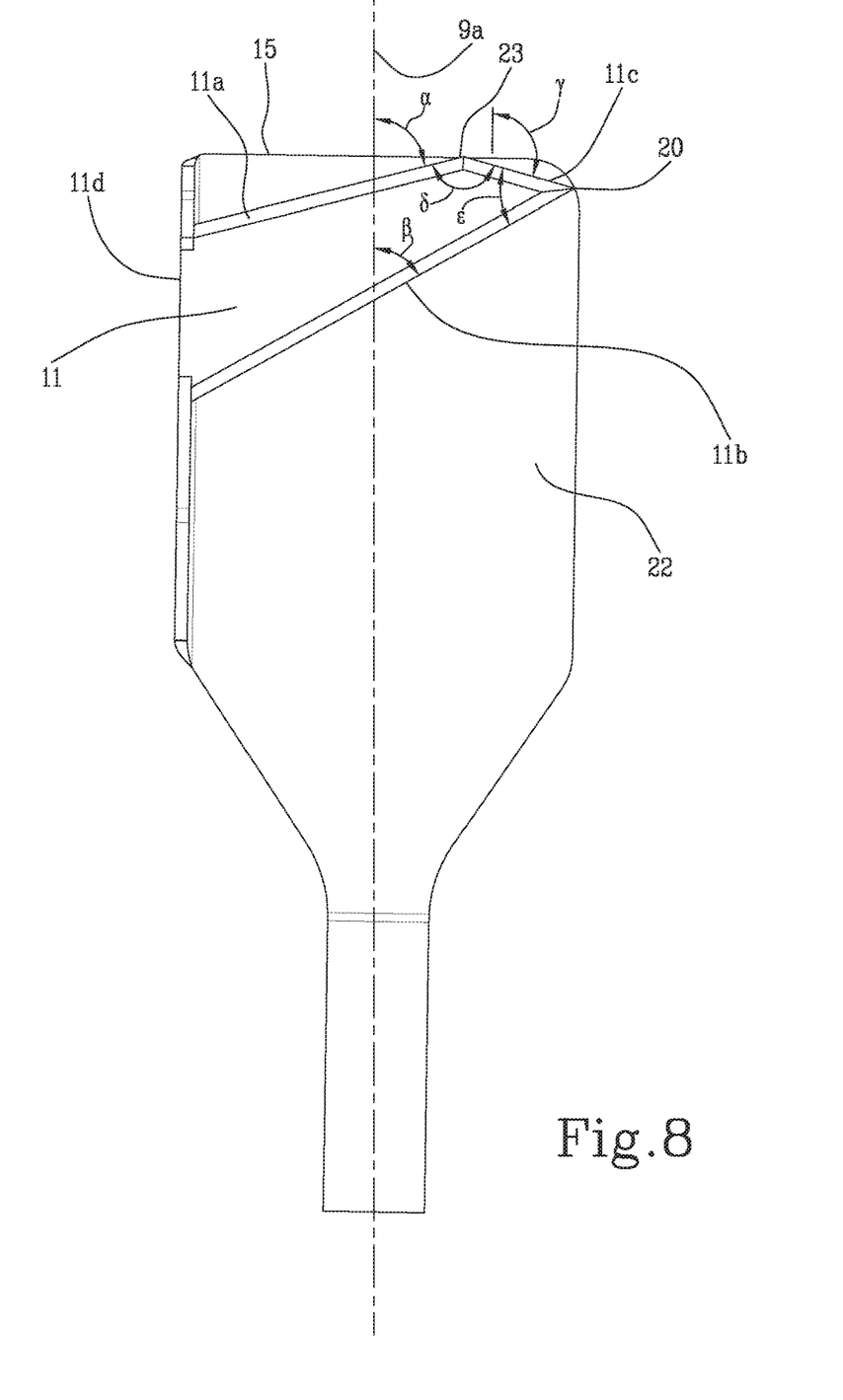
FIG. 8 is a rear view of the portion of the cutting tool shown in FIG. 7.

As shown in FIG. 8, the first distal cutting edge 11a forms an angle δ comprised between 145° and 155°, preferably of 150°, with said third intermediate cutting edge 11c. A vertex 23 is thus defined, which identifies a first V-shaped edge.

The second proximal cutting edge 11b, on the other hand, forms an angle ε comprised between 40° and 50°, preferably of 45°, with the third intermediate cutting edge 11c. A vertex 20 is thus defined, which identifies a second V-shaped edge.

The base plate 10 and the blade 11 are connected to each other only by means of a side wall 12, orthogonal to both and projecting from one side 13 of the base plate 10.

The blade 11 therefore has only one end 11d connected to the side wall 12, while the three cutting edges 11a, 11b and 11c are free.

The blade 11 is used to cut the strip of tendon at the bottom to be removed.

The width L of the cut is defined by the distance between the vertex 20 of the angle ε, formed by the third intermediate cutting edge 11c with the second cutting edge 11b, and the inner face 21 of the side wall 12.

The height h of the cut is defined, on the other hand, by the distance between the lower inner face 22 of the base plate 10 and the upper inner face 24 of the blade 11.

To facilitate the stripping of the soft tissue as the tool advances, the cutting head 9 has a beveled upper edge 14, located at the distal end 10d of the base plate 10, equipped with a blade 15, adapted to cutting the strip of tendon at the top.

The upper blade 15 and its beveled profile facilitate the insertion and advancement of the tool and the stripping of the soft tissue as the tool advances inside the surgical site.

In other words, the front bevel of the upper blade 15 placed in the frontal position helps to lift the soft tissue at the top of the tendon, facilitating the sliding of the tool because the inclination of the blade progressively affects the tendons with less effort from the surgeon.

The vertex 20 located at the angle ε of the blade 11, formed by the second proximal cutting edge 11b and by the third intermediate cutting edge 11c, is used to insert the tool into the desired soft tissue.

The V-shaped vertex 20 is oriented in the opposite direction to the edge 11d of the blade 11.

To assist in the incision process, the blade 11 has the other V-shaped vertex 23, at the angle δ, formed between the first distal cutting edge 11a and the third intermediate cutting edge 11c. This last V-angled edge helps to advance the tool.

This last vertex 23 is oriented in the proximal direction, in other words, along the direction in which the tool advances.

Therefore, a combination of angular V-shaped edges, i.e. the first and second vertex 23 and 20, and the inclination of the first cutting edge 11a and of the second cutting edge 11b with respect to the longitudinal axis 9a of the cutting head 9 (i.e. with respect to the proximal direction of advancing) improves the tool's cutting efficiency in both the proximal and distal directions, thanks to the two V-shaped edges on the blade 11.

The angle of the edges with respect to the working direction of the blade 11 significantly improves the cutting capacity of the tool.

The cutting edges 11a, 11b and 11c of the blade are also beveled.

In section, the cutting head 9 has a C-shape (in use).

The stem 2 has, in a distal position, a fitting 16 inclined with respect to the longitudinal axis 2a of an angle σ comprised between 10° and 20°, preferably of 15°.

This fitting 16 connects the stem 2 to the cutting head 9.

Following the inclination of the fitting 16, to which the cutting head 9 is joined, in use the cutting head 9 is positioned below the longitudinal axis 2a of the stem 2.

The position and inclination of the cutting head with respect to the longitudinal axis 2a facilitate the insertion and use of the tool on the upper edge of the patella. The position of the stem 2 and of the cutting head 9 on staggered planes ensures that the stem does not touch the tendon during cutting.

The cutting head 9 has a projection 17 that is inserted into a slot 18 during the production of the tool itself.

The projection 17 is also inclined with respect to the longitudinal axis 9a of the cutting head 9 by an angle Ω having the same width as the above angle α, i.e. comprised between 10° and 20°, preferably of 15°.

The two parts are then firmly coupled together, so that the stem 2 and cutting head 9 are a single indivisible body.

Figure 1:
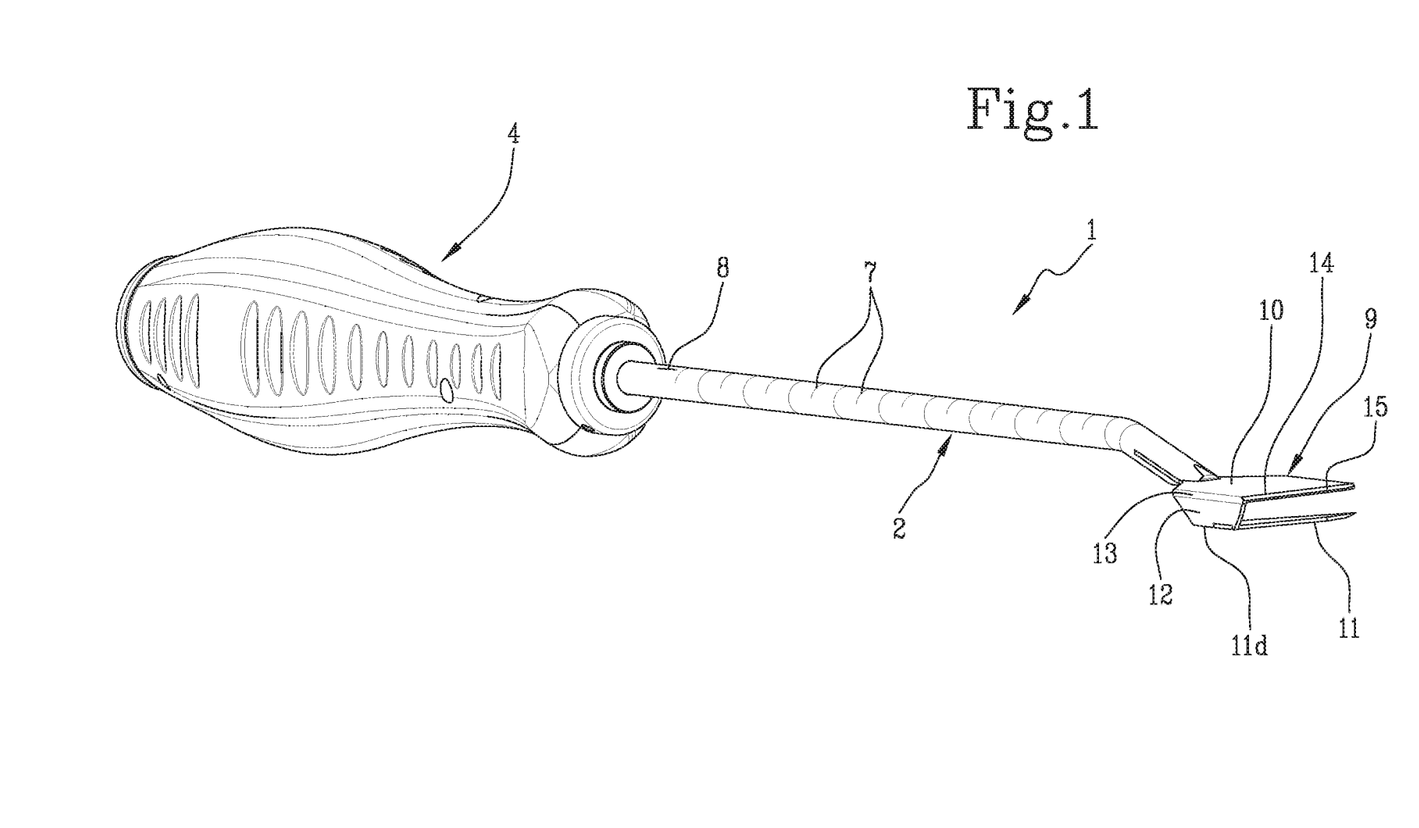
FIG. 1 shows a perspective view of a cutting tool for the horizontal incision of a tendon in accordance with the present invention.
Figure 2:
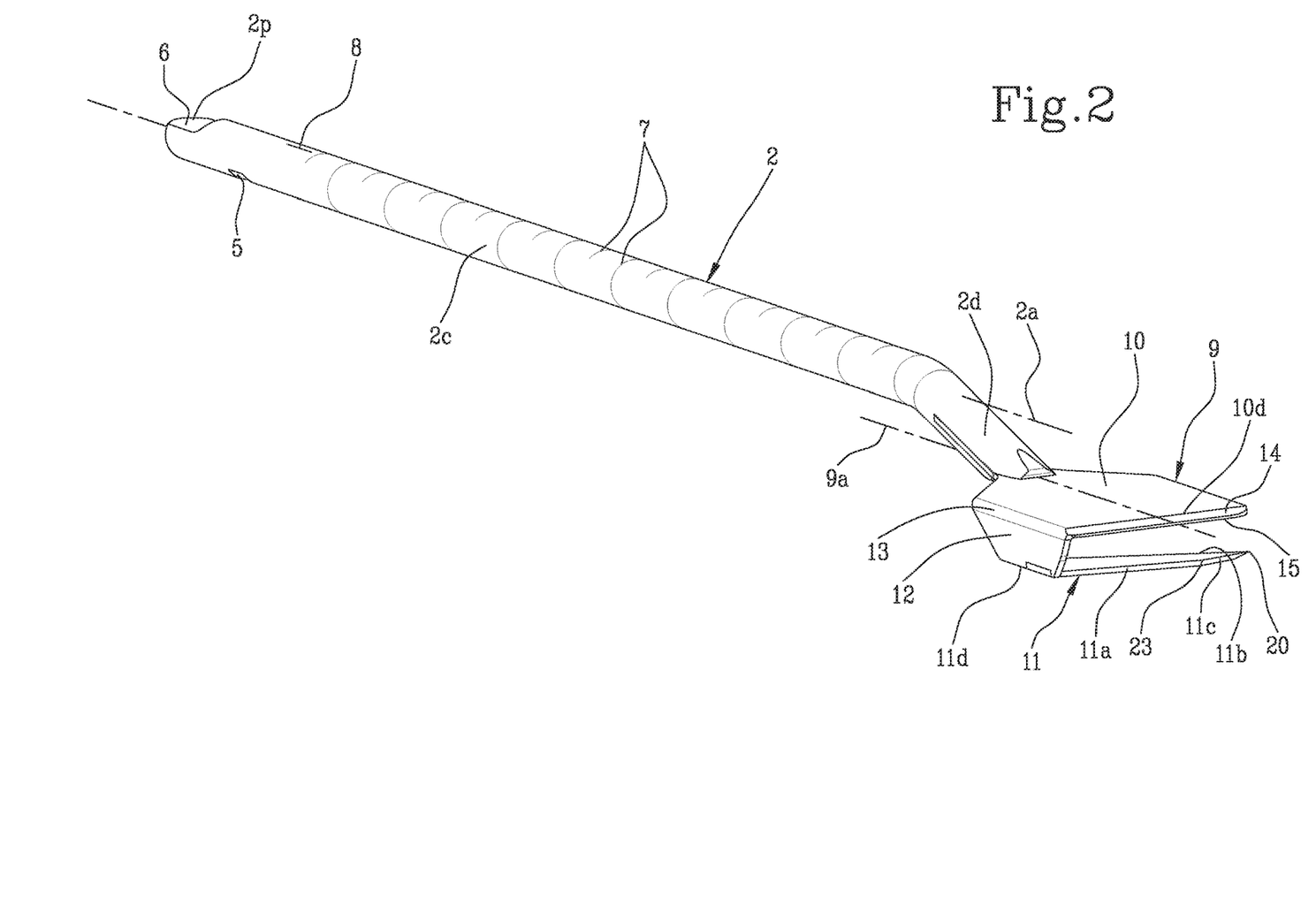
FIG. 2 shows a perspective view of a portion of the cutting tool shown in FIG. 1.
Figure 3:
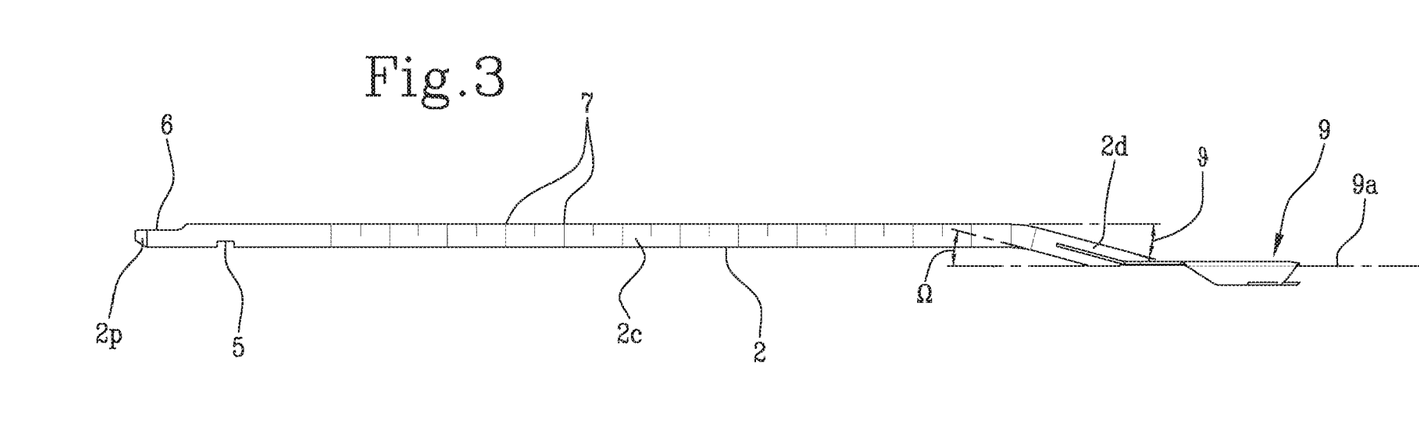
FIG. 3 is a side view of the cutting tool that is the subject of the present invention, as illustrated in FIG. 2.
Figure 4:
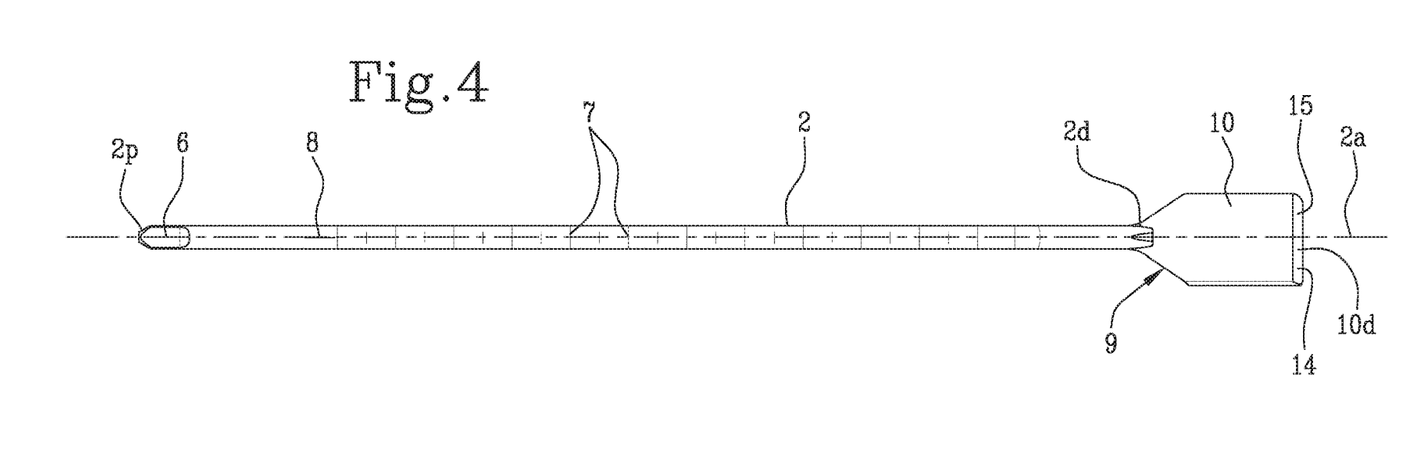
FIG. 4 is a top view of the cutting tool that is the subject of the present invention, as illustrated in FIG. 2.
Figure 5:
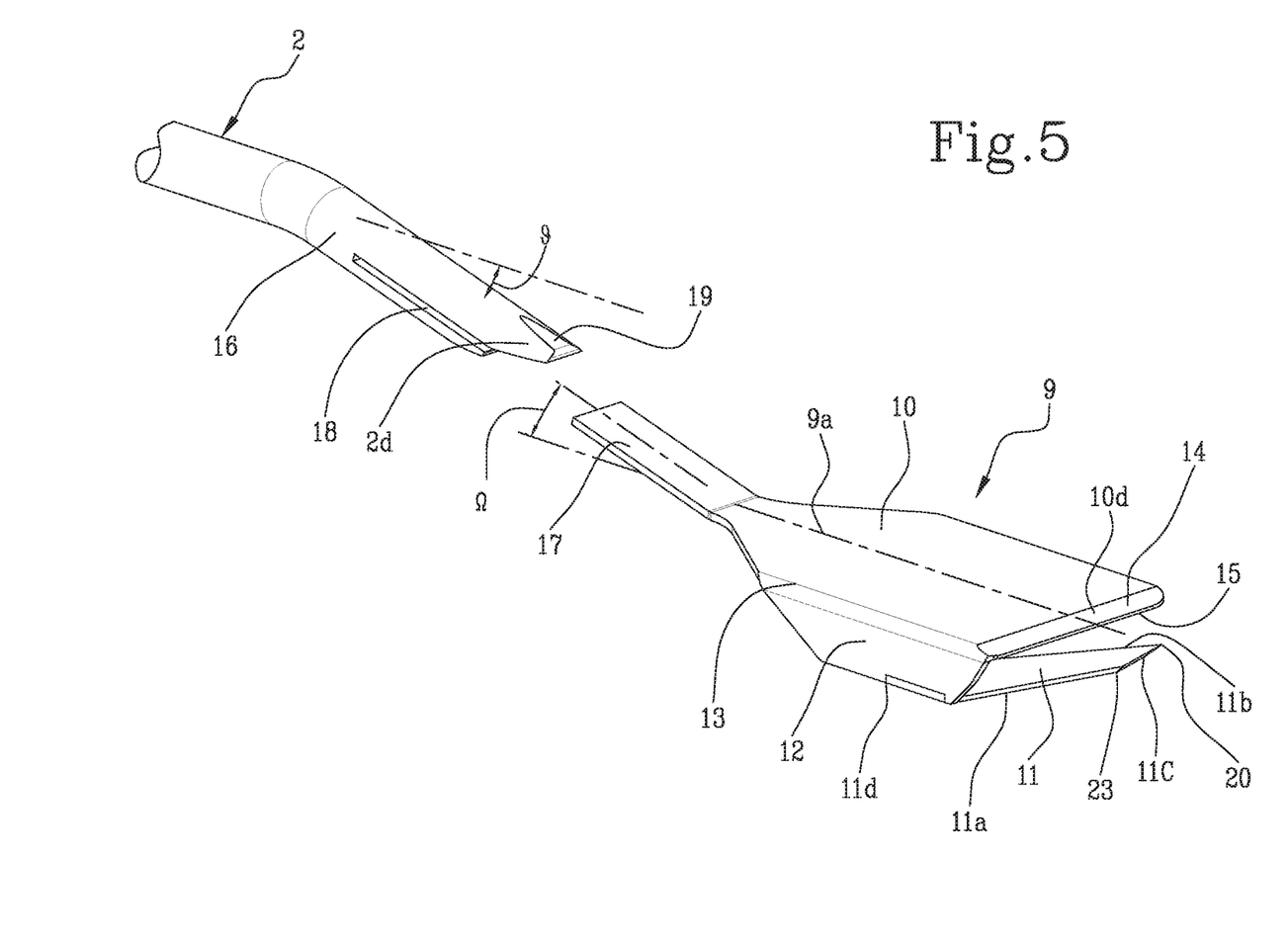
FIG. 5 is an exploded view of a part of the cutting tool that is the subject of the present invention, illustrated in a production step.
Figure 6:
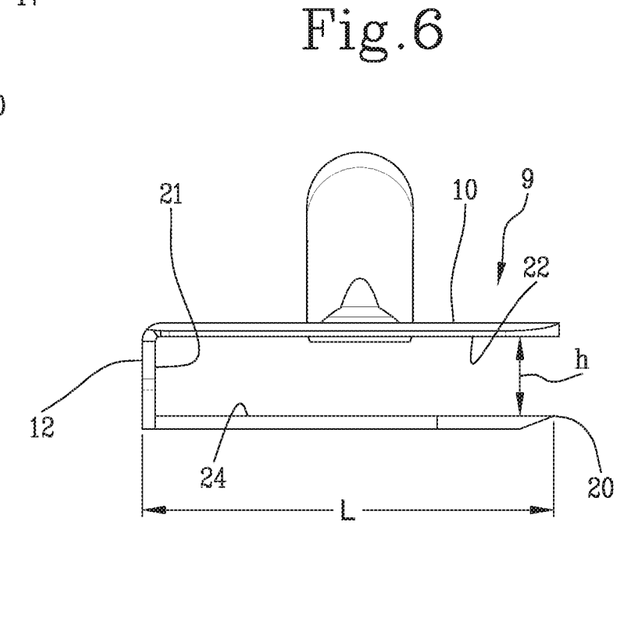
FIG. 6 is a frontal view of the cutting tool that is the subject of the present invention, as illustrated in FIG. 2.
Figure 7:
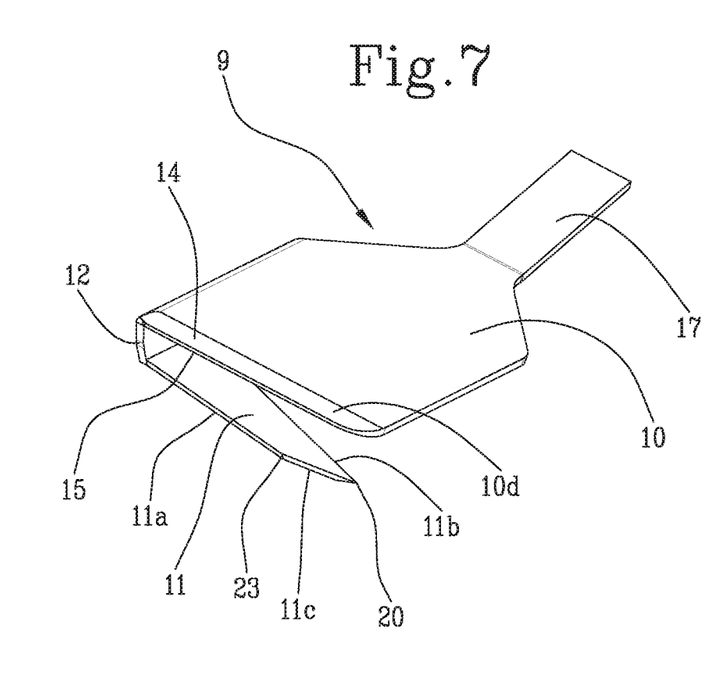
FIG. 7 is a perspective view of a portion of the cutting tool that is the subject of the present invention.

This type of coupling further stabilises the cutting head 9 with the stem 2. Moreover, as shown in FIG. 5 where the cutting head 9 is represented as separated from the stem 2 as it is before the end of the production process, the stem 2 has, at the distal end 2d, a nose 19 that increases the steadiness of the tool itself because it acts as a rigid vertical stop for the cutting head 9 during use, operating precisely at the point of connection between the cutting head 9 and the stem 2.

During operation, the cutting tool 1 is inserted axially into the dedicated grip, or gripping handpiece 4, for axial collection of the soft tissue.

The tip of the cutting blade of the tool 1 must be inserted sideways into the desired soft tissue for collection.

Once inserted, the cutting tool 1 must be advanced in the proximal direction through the soft tissue, so as to cut the thickness of the strip of soft tissue with a predefined width and height. The tool is advanced to the pre-established depth, which can be controlled through the graduated scale 7 on the stem 2.

The V-shaped, double-edged cutting blade allows for an improved and less resistant transition in both forward and reverse directions.

The advantages obtained with this tool are better handling and steadiness of the tool thanks to the single unit design, with the cutting head firmly connected to the stem, as well as improved cutting in the proximal and distal direction thanks to the double V-shaped blade design and the inclination of the distal and proximal edges with respect to the longitudinal axis of the cutting head.

The offset position between the stem and cutting head and the inclination between the fitting and the stem facilitate the insertion of the tool at the upper edge of the patella.

The distal bevel of the upper blade helps advance the tool as a result of its improved capacity for stripping soft tissue.

The tool is, thus, simple to use. The length of surgery is considerably reduced thanks to the greater smoothness of the tool and the easier stripping of the soft tissue.

The tool thus created and designed improves the steadiness of cutting by reducing the probability of an unacceptable collection of the tendon.

The particular geometry of the blade, with the blades not perpendicular to the direction in which the tool advances, increases its capacity for cutting backwards and forwards, overcoming the drawbacks encountered in the known art.

The invention claimed is:

1. A cutting tool for a horizontal incision of tendons, the cutting tool comprising:
   a stem extending along a longitudinal axis, the stem having a distal end and a proximal end, and
   a cutting head, located close to said distal end, the cutting head having a base plate, the base plate having a longitudinal extension axis parallel to the longitudinal axis of said stem, and a blade extending on a plane parallel to said base plate, wherein said blade has a plurality of cutting edges inclined with respect to said longitudinal extension axis of said base plate according to different angles, so as to identify at least two vertices defined by two V-shaped profiles, wherein the plurality of cutting edges is inclined on the plane parallel to said base plate.

2. The cutting tool according to claim 1, wherein said blade comprises a first distal cutting edge inclined with respect to the longitudinal extension axis of said cutting head base plate by an angle between 70° and 80°, a second proximal cutting edge inclined with respect to the longitudinal extension axis of said base plate by an angle between 55° and 65°, and a third intermediate cutting edge, interposed between the first distal cutting edge and the second proximal cutting edge and connected thereto, inclined with respect to the longitudinal extension axis of said base plate by an angle between 100° and 110°.

3. The cutting tool according to claim 2, wherein said first distal cutting edge forms an angle between 145° and 155°, with said third intermediate cutting edge.

4. The cutting tool according to claim 3, wherein the angle formed by first distal cutting edge and the third intermediate cutting edge is 150°.

5. The cutting tool according to claim 2, wherein said second proximal cutting edge forms an angle between 40° and 50°, with said third intermediate cutting edge.

6. The cutting tool according to claim 5, wherein the angle formed by the second proximal cutting edge and the third intermediate cutting edge is 45°.

7. The cutting tool according to claim 2, wherein said base plate and said blade are connected to each other only by a side wall orthogonal to both of them and projecting on one side of said base plate.

8. The cutting tool according to claim 7, wherein the base plate of said cutting head lies on a plane parallel to the longitudinal axis of said stem and is connected to the stem by means of a fitting inclined with respect to the longitudinal axis of said stem by an angle between 10° and 20°.

9. The cutting tool according to claim 8, wherein said cutting head, in use configuration, is located below the longitudinal axis of the stem.

10. The cutting tool according to claim 9, wherein said cutting head has a C-shaped cross-section in use configuration.

11. The cutting tool according to claim 8, wherein the angle of incline of the fitting is 15°.

12. The cutting tool according to claim 2, wherein the angle of incline of the first distal cutting edge is 75°, the angle of incline of the second proximal cutting edge is 60°, and the angle of incline of the third intermediate cutting edge, is 105°.

13. The cutting tool according to claim 1, wherein said cutting head has a beveled upper edge, located at a distal end of the base plate, comprising a blade adapted to cut a top of a tendon strip.

14. The cutting tool according to claim 1, wherein said stem is integral with said cutting head.

15. The cutting tool according to claim 1, wherein the cutting tool can be coupled to a gripping handpiece.

16. The cutting tool according to claim 15, wherein said stem has a notch for the steady coupling to said gripping handpiece.

17. The cutting tool according to claim 15, wherein said stem has a flat surface to avoid relative rotation between the stem and the gripping handpiece.

18. The cutting tool according to claim 1, wherein said stem has a graduated scale.

19. The cutting tool according to claim 1, wherein said stem has an orientation indicator to aid a correct alignment with a gripping handpiece and a correct insertion of the cutting tool into a surgical site.

* * * * *